United States Patent
Barthelmes et al.

(10) Patent No.: US 12,359,270 B2
(45) Date of Patent: Jul. 15, 2025

(54) MEDICAL INSTRUMENT AND METHOD FOR PRODUCING A MEDICAL INSTRUMENT

(71) Applicant: Aesculap AG, Tuttlingen (DE)

(72) Inventors: Sven Barthelmes, Emmingen-Liptingen (DE); Dominic Faitsch, Neuhausen (DE); Stefanie Schabert, Aldingen (DE)

(73) Assignee: AESCULAP AG, Tuttlingen (DE)

( * ) Notice: Subject to any disclaimer, the term of this patent is extended or adjusted under 35 U.S.C. 154(b) by 846 days.

(21) Appl. No.: 17/410,246

(22) Filed: Aug. 24, 2021

(65) Prior Publication Data
US 2021/0381071 A1     Dec. 9, 2021

Related U.S. Application Data

(63) Continuation of application No. PCT/EP2020/055431, filed on Mar. 2, 2020.

(30) Foreign Application Priority Data

Mar. 1, 2019   (DE) .................. 10 2019 105 268.8

(51) Int. Cl.
*A61B 17/00*     (2006.01)
*A61B 17/06*     (2006.01)
(Continued)

(52) U.S. Cl.
CPC .......... *C21D 7/02* (2013.01); *A61B 17/06061* (2013.01); *A61B 17/3201* (2013.01);
(Continued)

(58) Field of Classification Search
CPC ........................... A61B 17/28; A61B 2017/28
See application file for complete search history.

(56) References Cited

U.S. PATENT DOCUMENTS

| | | | |
|---|---|---|---|
| 1,990,694 A  * | 2/1935 | Jacobs | ................. C22C 19/002 |
| | | | 72/340 |
| 2,305,156 A | 12/1942 | Grubel | |

(Continued)

FOREIGN PATENT DOCUMENTS

| | | |
|---|---|---|
| CN | 105326563 A | 2/2016 |
| CN | 107536634 A | 1/2018 |

(Continued)

OTHER PUBLICATIONS

Entgraten: Massnahmen und Methoden, Entgraten in Umformtechnik: Beschreibung, Trends und Umsetzung, Institut fuer Integrierte Produktion Hannover, Nov. 5, 2018, https://www.iph-hannover.de/de/information/umf ormtechnik/entgraten/, retrieved Jan. 31, 2020, with translation, 15 pages.

(Continued)

*Primary Examiner* — Jacob J Cigna
(74) *Attorney, Agent, or Firm* — Christopher A. Rothe; CM Law

(57) ABSTRACT

A medical instrument and method for producing a medical instrument with at least one instrument body part made from an instrument body part blank by forming. The at least one instrument body part has at least one deburring face formed by milling. The at least one deburring face includes one or more portions. Each portion extends perpendicularly to a machining plane. A normal to the machining plane defines a deburring longitudinal axis.

15 Claims, 8 Drawing Sheets

Figure 1:
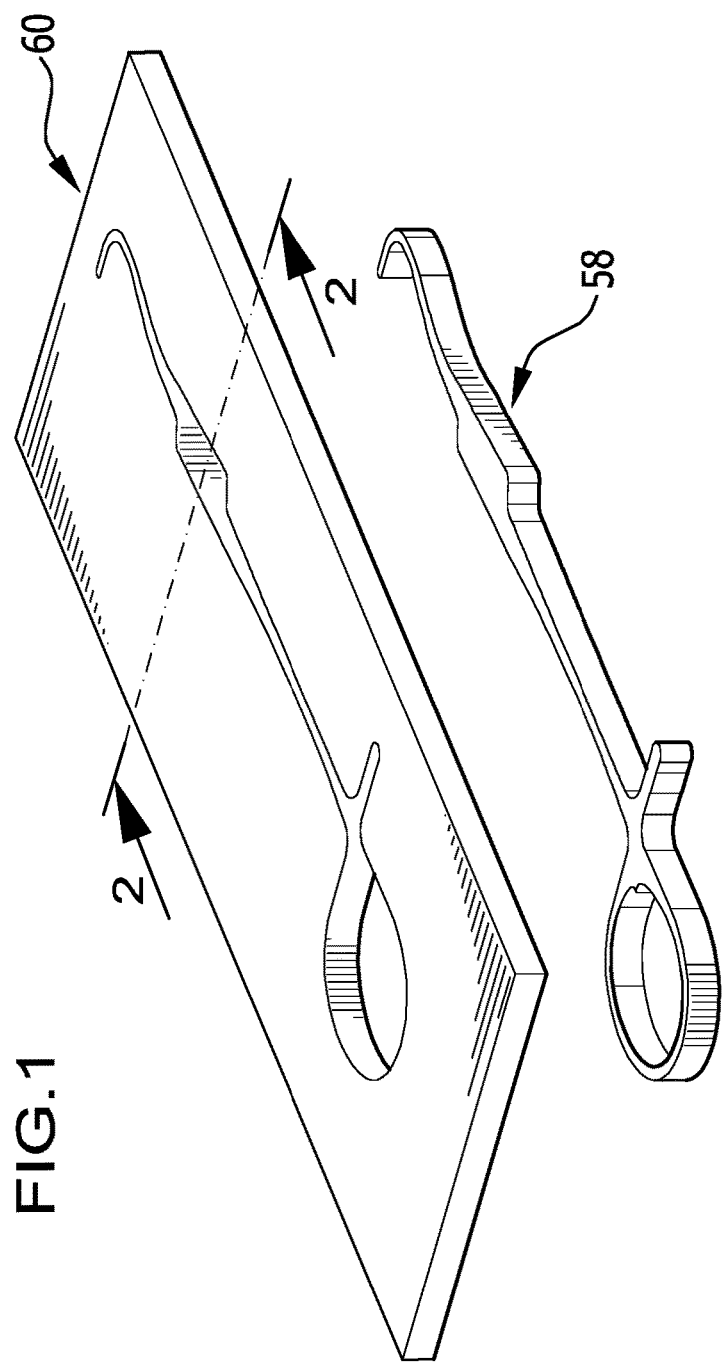

(51) Int. Cl.
*A61B 17/3201* (2006.01)
*B23C 3/12* (2006.01)
*B24B 1/04* (2006.01)
*B24B 3/60* (2006.01)
*C21D 7/02* (2006.01)

(52) U.S. Cl.
CPC ............... *B23C 3/12* (2013.01); *B24B 1/04* (2013.01); *B24B 3/605* (2013.01); *A61B 2017/00526* (2013.01)

(56) References Cited

U.S. PATENT DOCUMENTS

| | | | | |
|---|---|---|---|---|
| 3,646,939 | A | * | 3/1972 | Sklar ............... A61B 17/282 |
| | | | | 606/207 |
| 3,911,766 | A | * | 10/1975 | Fridolph ............ B23K 9/007 |
| | | | | 606/208 |
| 3,952,749 | A | | 4/1976 | Fridolph et al. |
| 5,083,008 | A | | 1/1992 | Zerver |
| 5,298,115 | A | | 3/1994 | Leonard |
| 8,176,813 | B2 | * | 5/2012 | Hu ..................... B25B 13/04 |
| | | | | 76/114 |
| 9,398,912 | B1 | | 7/2016 | Samaraweera |
| 2009/0214312 | A1 | | 8/2009 | Geisel |
| 2016/0030105 | A1 | | 2/2016 | Mayer et al. |
| 2017/0020571 | A1 | | 1/2017 | Hawkes et al. |
| 2018/0000536 | A1 | | 1/2018 | Becker et al. |
| 2020/0383695 | A1 | | 12/2020 | Weisshaupt et al. |

FOREIGN PATENT DOCUMENTS

| | | | |
|---|---|---|---|
| CN | 107962391 A | 4/2018 | |
| CN | 108015599 A | 5/2018 | |
| DE | 2521487 A1 | 11/1975 | |
| DE | 3506866 C * | 9/1986 | ............... B23C 3/12 |
| DE | 3506866 C1 | 9/1986 | |
| DE | 10141714 A1 | 3/2003 | |
| EP | 0416296 A1 | 3/1991 | |
| EP | 2093002 A2 | 8/2009 | |
| JP | H08084734 A | 4/1996 | |
| JP | 2018057498 A | 4/2018 | |
| WO | 2018166989 A1 | 9/2018 | |

OTHER PUBLICATIONS

Search Report received in International Application No. PCT/EP2020/055431 dated Jun. 24, 2020, with translation, 5 pages.

* cited by examiner

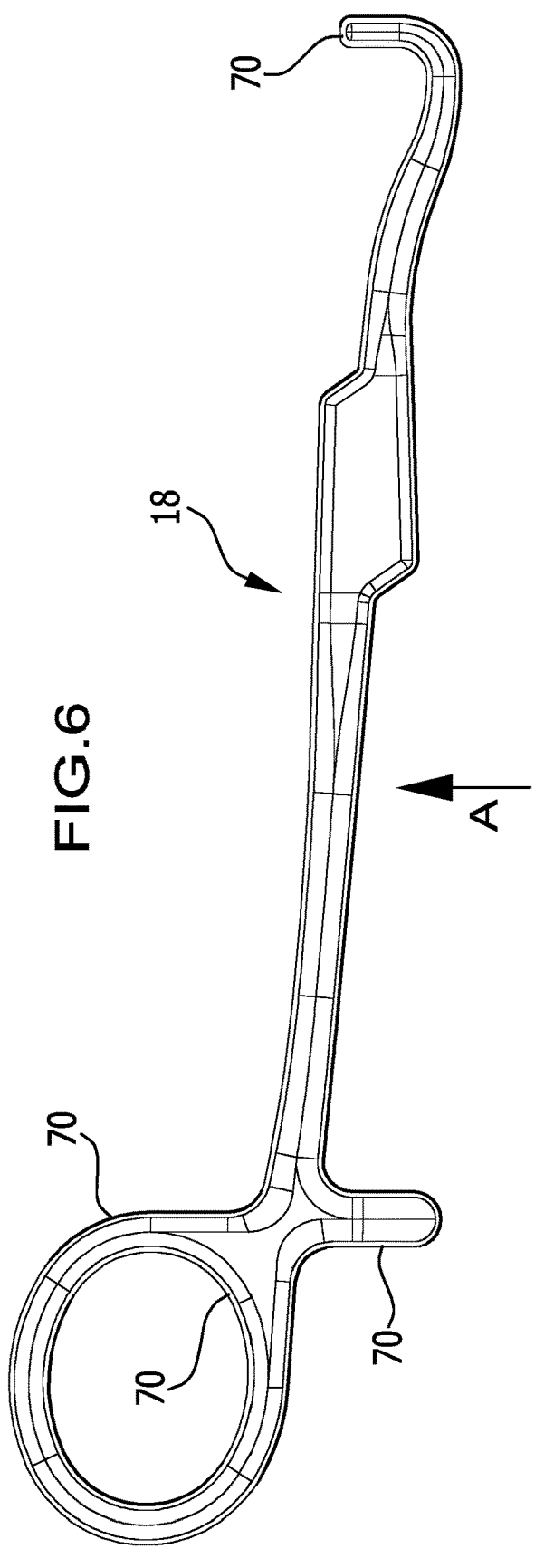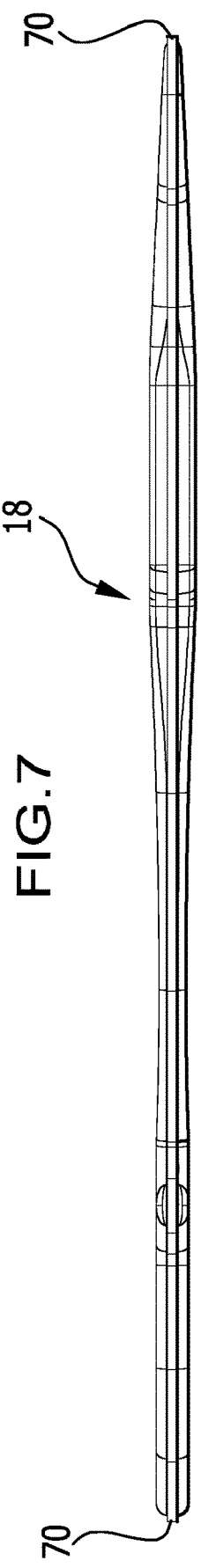

MEDICAL INSTRUMENT AND METHOD FOR PRODUCING A MEDICAL INSTRUMENT

CROSS-REFERENCE TO RELATED APPLICATIONS

This application is a continuation of International Application No. PCT/EP2020/055431, filed on Mar. 2, 2020, and claims the benefit of priority of German Application No. 10 2019 105 268.8, filed on Mar. 1, 2019. The contents of International Application No. PCT/EP2020/055431 and German Application No. 10 2019 105 268.8 are incorporated herein by reference in their entireties and for all purposes.

FIELD

The present disclosure relates to medical instruments generally, and more specifically to a medical instrument with at least one instrument body part, wherein the at least one instrument body part is made from an instrument body part blank by forming.

Further, the present disclosure relates to methods for producing medical instruments generally, and more specifically to a method for producing a medical instrument, which comprises at least one instrument body part, in which method an instrument body part blank is reshaped and burrs that are created during forming, in particular due to tolerance and process fluctuations, are removed.

BACKGROUND

In particular, medical instruments with two instrument body parts that are pivotably mounted on one another are known. The instrument body parts of such instruments are made, in particular, by forming from a blank, also referred to in the following as instrument body part blank. Protruding or projecting burrs are thereby created. These burrs are conventionally removed by hand-guided belt grinding.

The disadvantage in the production of known medical instruments is, in particular, that form and dimensional fluctuations may arise as a result of hand-guided machining processes. In addition, an undefined heat input into the instrument body part reshaped from the instrument body part blank may occur when the burrs that were created during forming are removed by belt grinding, in particular in a hand-guided manner.

SUMMARY

In a first aspect of the disclosure, a medical instrument with at least one instrument body part is provided. The at least one instrument body part is made from an instrument body part blank by forming. The at least one instrument body part has at least one deburring face formed by milling, in particular by machine milling. The at least one deburring face comprises one or more portions. Each portion of the at least one deburring face extends perpendicularly to a common machining plane. A normal to the machining plane defines a deburring longitudinal axis. The at least one deburring face extends in parallel to the deburring longitudinal axis. The medical instrument forms scissors, a plier, a needle holder or a clamp, and comprises two instrument body parts, wherein the two instrument body parts are mounted on one another so as to be pivotable about a pivot axis, and wherein the pivot axis defines the deburring longitudinal axis.

In a second aspect of the disclosure, a method for producing a medical instrument is provided, wherein the medical instrument comprises at least one instrument body part. In said method an instrument body part blank is reshaped and burrs that were created during forming, in particular due to tolerance and process fluctuations, are removed. The burrs are removed by milling, in particular machine milling. The at least one instrument body part is held during milling. A milling tool, for the purpose of removing the burrs, is rotated about a deburring longitudinal axis and, for the purpose of creating at least one deburring face, is moved in a machining plane, the normal of which defines the deburring longitudinal axis, without changing an alignment of the deburring longitudinal axis relative to the machining plane. Formed on the at least one instrument body part is a joint bore with a bore longitudinal axis, said axis extending in parallel or substantially in parallel to the deburring longitudinal axis. At least two, in particular only two, instrument body parts are coupled to one another so as to be pivotable with one another about the bore longitudinal axis. The medical instrument is produced in form of scissors, a plier, a needle holder or a clamp.

BRIEF DESCRIPTION OF THE DRAWING FIGURES

Figure 2:
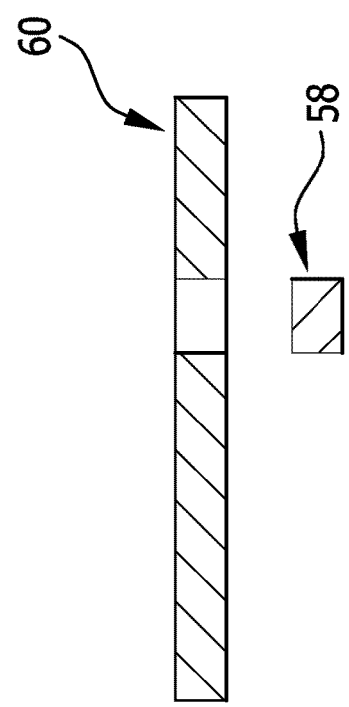
Figure 3:
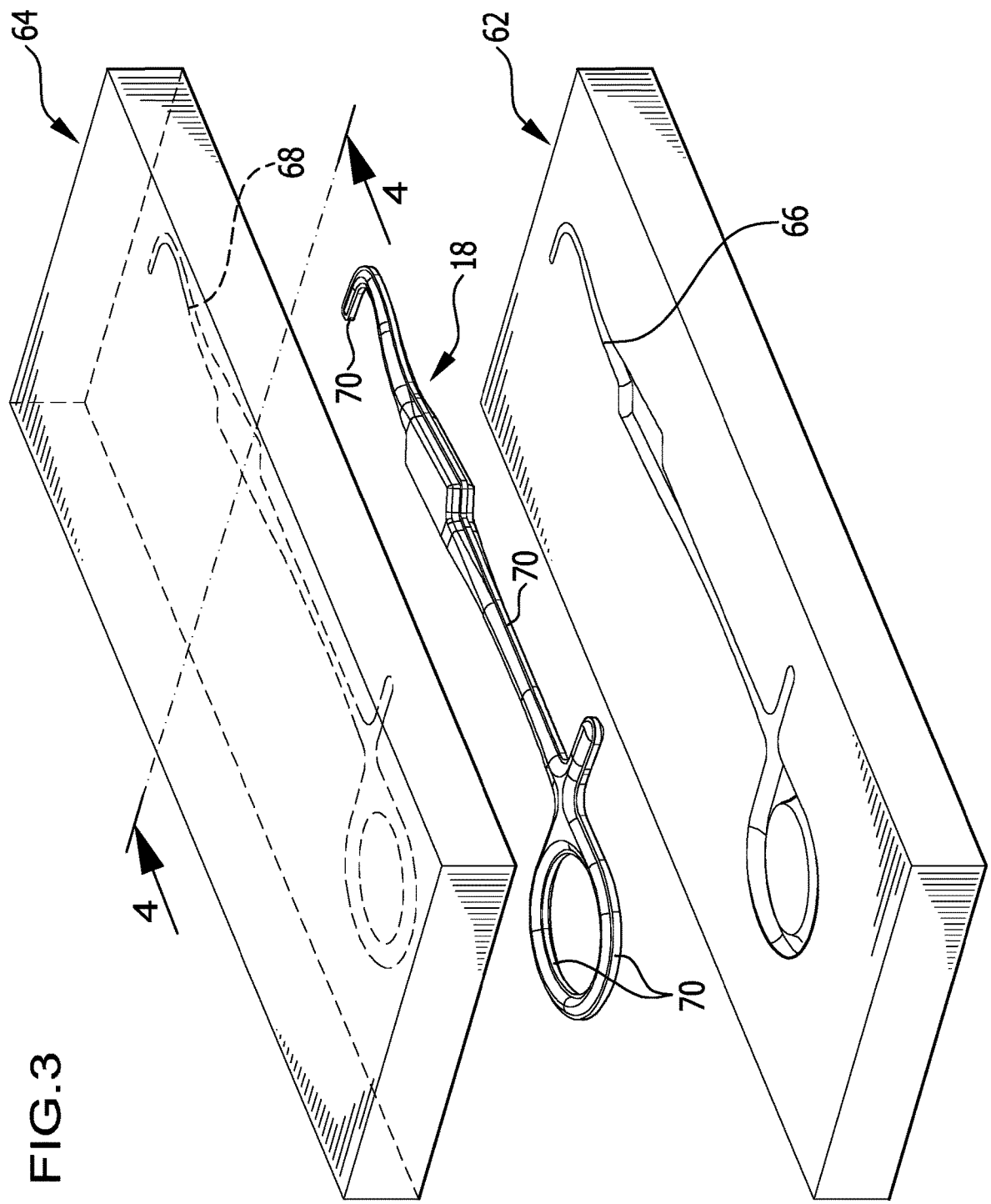
Figure 4:
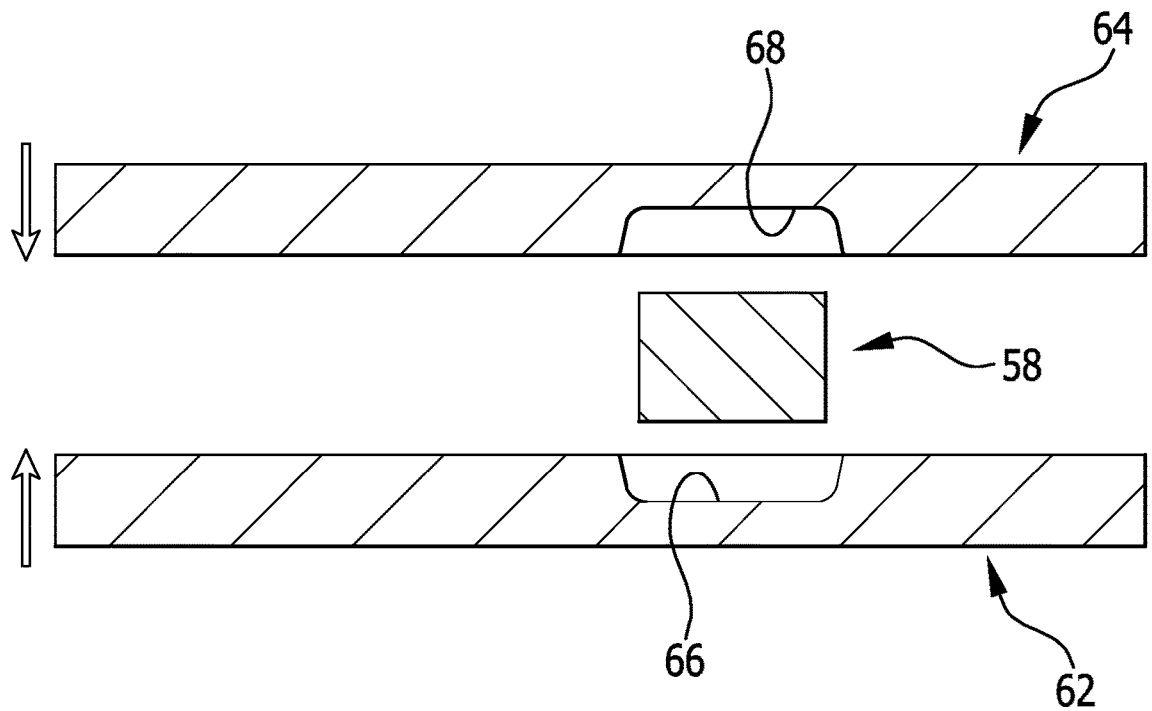
Figure 5:
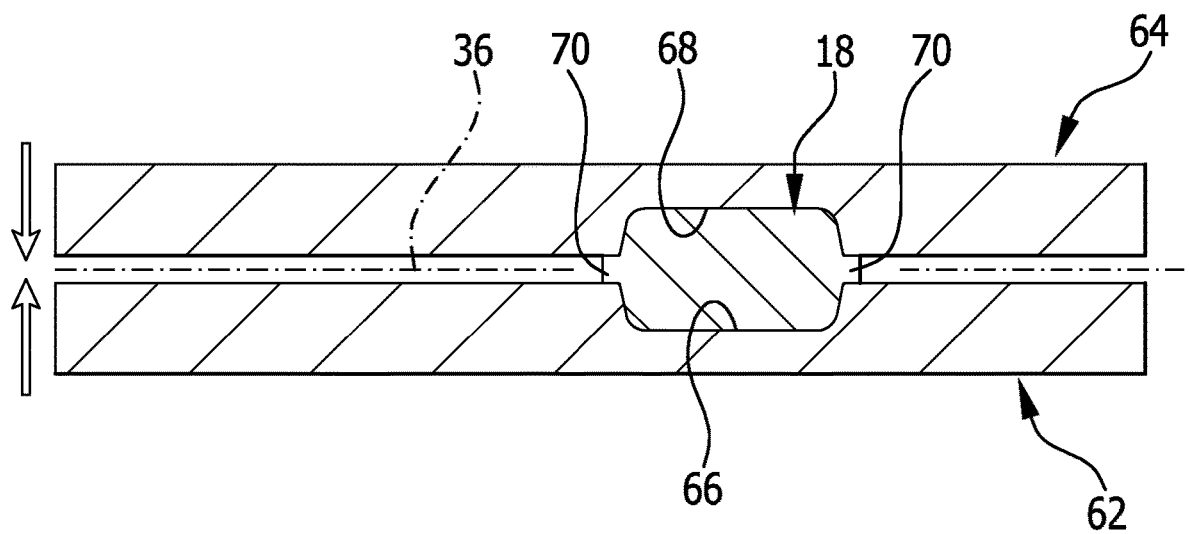
Figure 8:
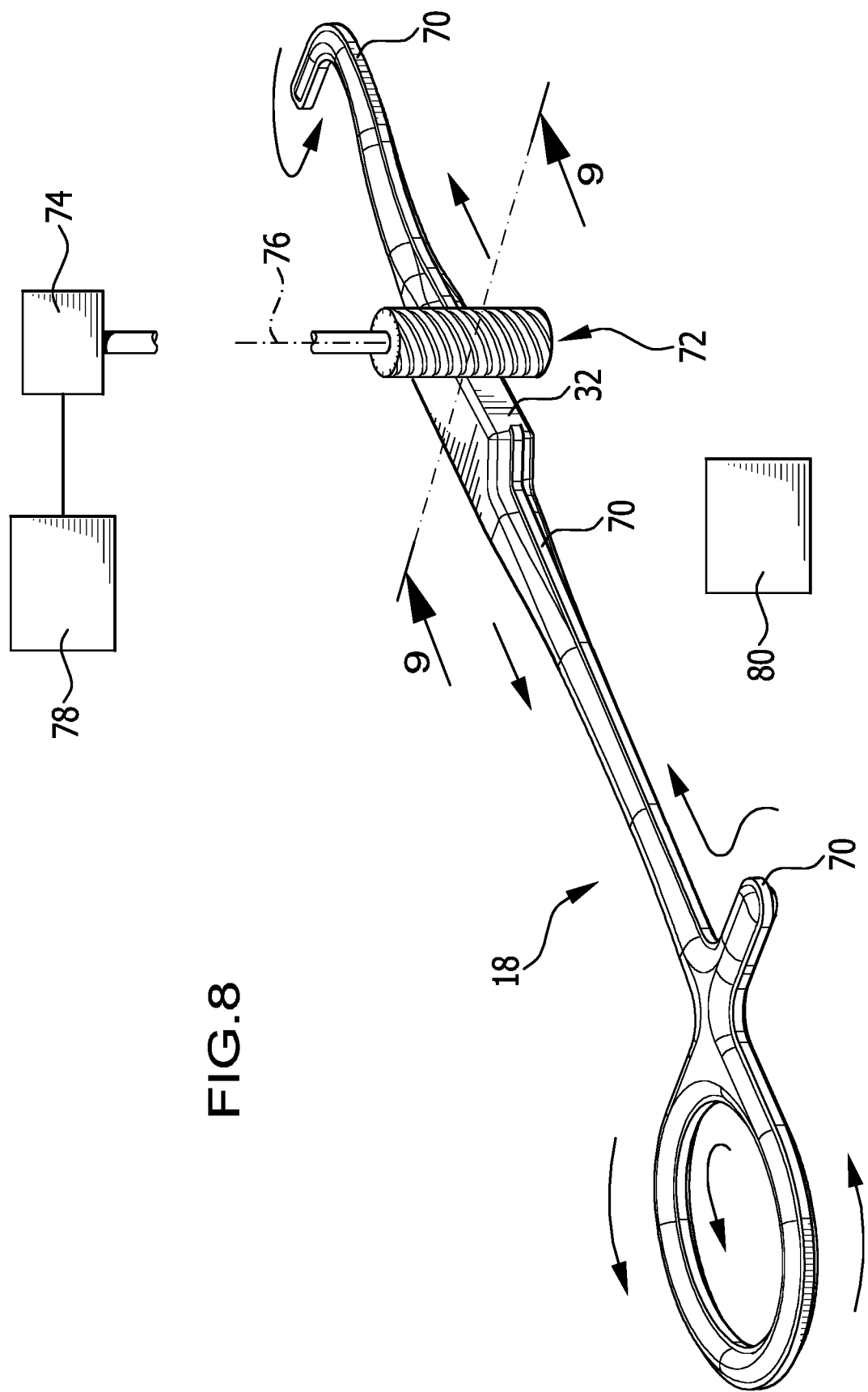
Figure 9:
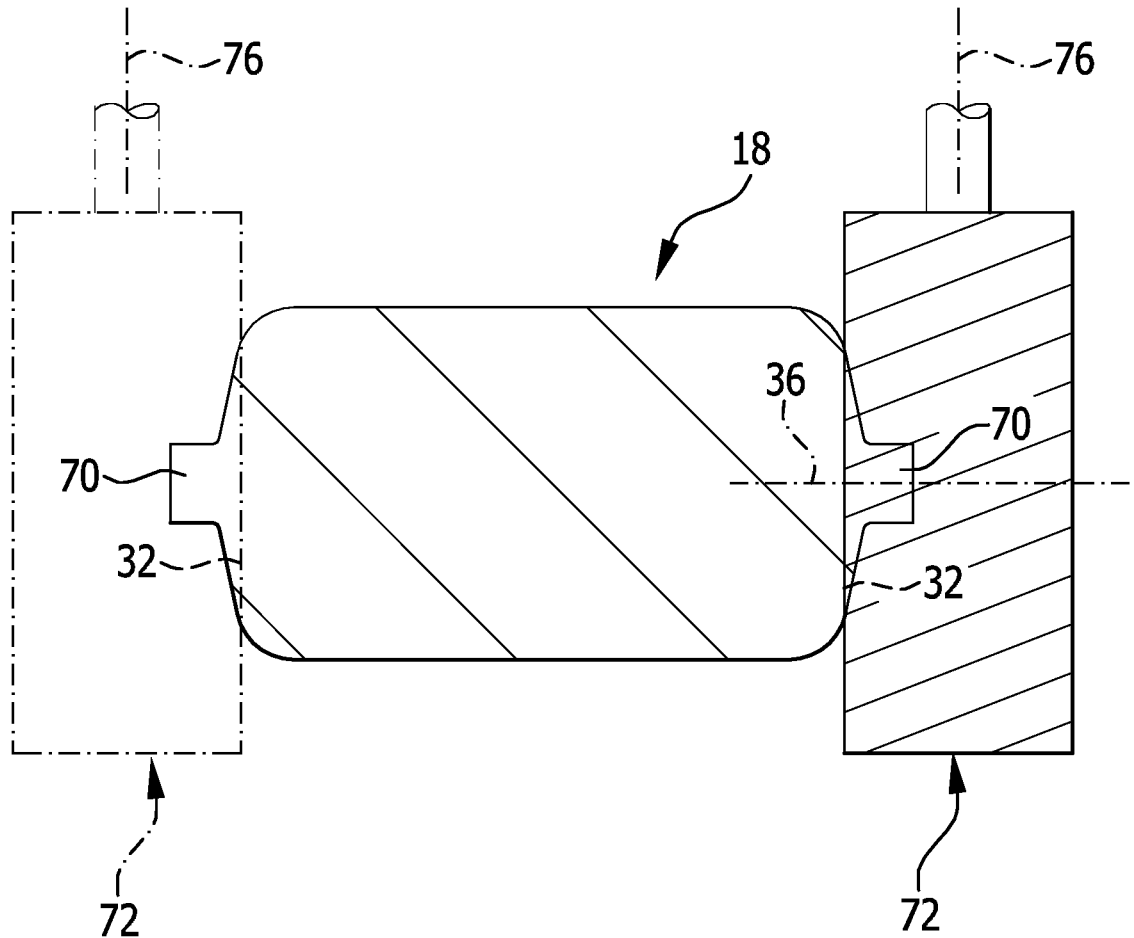
Figure 10:
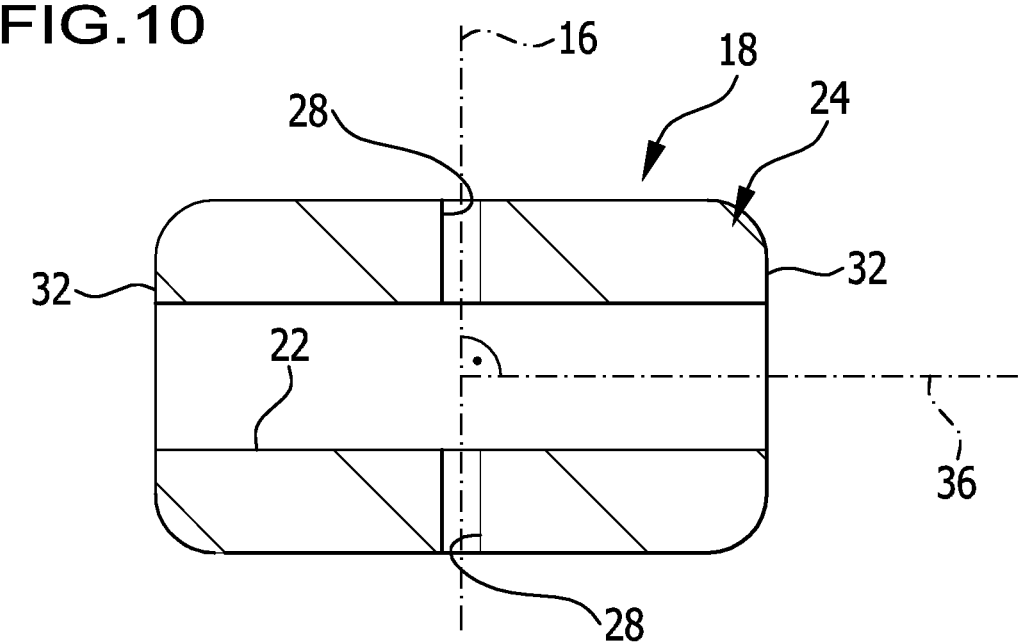
Figure 11:
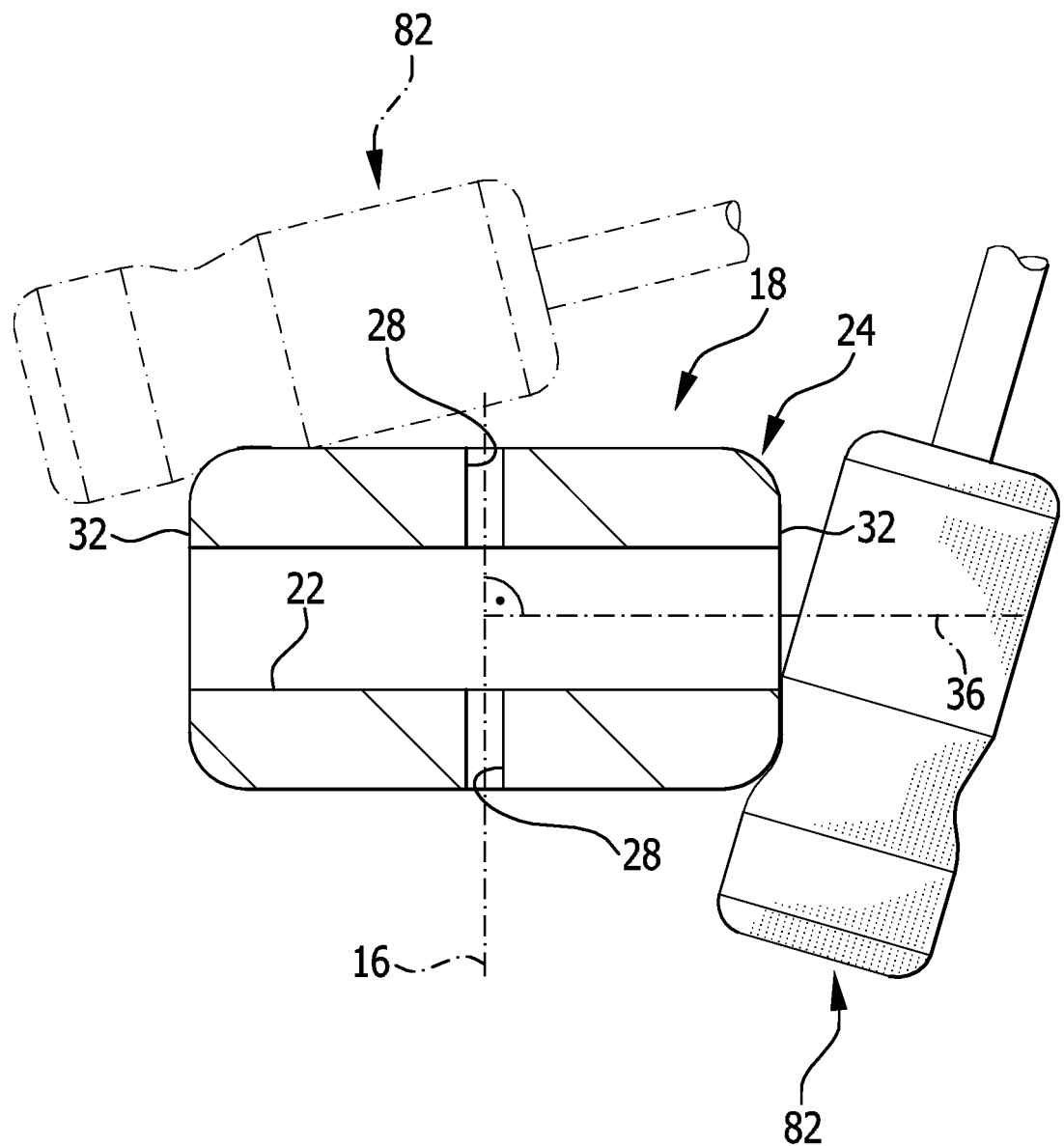
Figure 12:
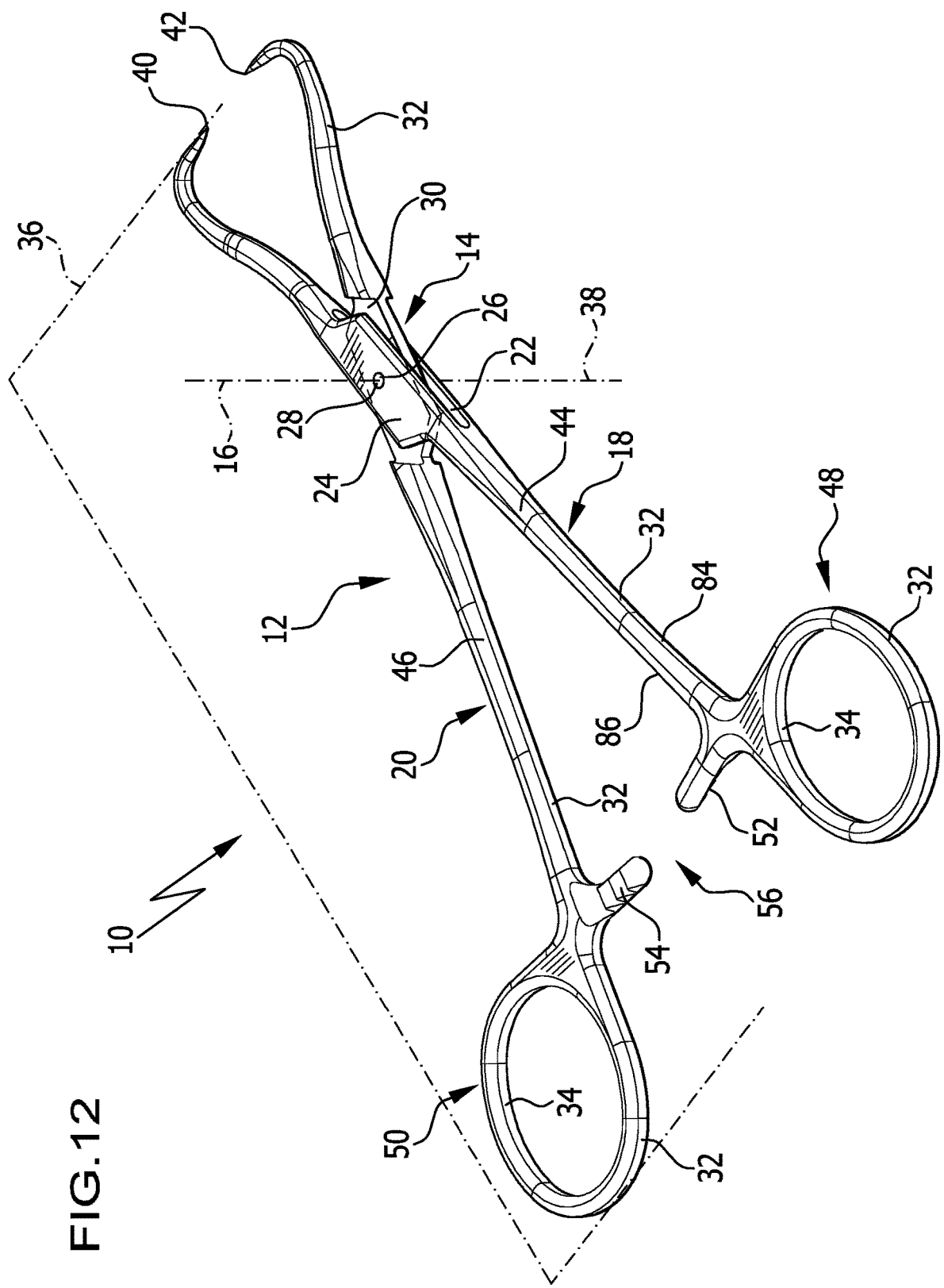

The foregoing summary and the following description may be better understood in conjunction with the drawing figures, of which:

FIG. 1: shows a schematic depiction of an embodiment of an instrument body part blank being punched out of a plate with a punching tool;

FIG. 2: shows a cut view along line 2-2 in FIG. 1;

FIG. 3: shows a schematic depiction of an embodiment of an instrument body part reshaped from an instrument body part blank upon removal from cooperating forming tools;

FIG. 4: shows a cut view along line 4-4 in FIG. 3 upon insertion of the instrument body part blank into the forming tools;

FIG. 5: shows a view analogous to FIG. 4 after the forming of the instrument body part blank by the cooperating forming tools;

FIG. 6: shows a plan view of the embodiment of an instrument body part depicted in FIG. 3;

FIG. 7: shows a view of the instrument body part from FIG. 6 in the direction of the arrow A;

FIG. 8: shows a schematic depiction of the instrument body part from FIGS. 6 and 7 upon machine deburring with a milling tool for forming deburring faces;

FIG. 9: shows a cut view along line 9-9 in FIG. 8;

FIG. 10: shows a cut view analogous to FIG. 9 after the formation of a push-through closure box and a joint bore on the instrument body part;

FIG. 11: shows a schematic depiction of the deburred instrument body part during polishing; and FIG. 12: shows a perspective total view of an embodiment of a medical instrument with two instrument body parts that are pivotably mounted on one another.

DETAILED DESCRIPTION

Although the disclosure is illustrated and described herein with reference to specific embodiments, the disclosure is not intended to be limited to the details shown. Rather, various modifications may be made in the details without departing from the disclosure.

The present disclosure relates to a medical instrument with at least one instrument body part, wherein the at least one instrument body part is made from an instrument body part blank by forming, wherein the at least one instrument body part has at least one deburring face formed by milling, in particular by machine milling, wherein the at least one deburring face comprises one or more portions, wherein each portion of the at least one deburring face extends perpendicularly to a common machining plane, wherein a normal to the machining plane defines a deburring longitudinal axis, and wherein the at least one deburring face extends in parallel to the deburring longitudinal axis, wherein the medical instrument forms scissors, a plier, a needle holder or a clamp, and comprises two instrument body parts, wherein the two instrument body parts are mounted on one another so as to be pivotable about a pivot axis, and wherein the pivot axis defines the deburring longitudinal axis.

Instrument body parts of medical instruments can be configured in a highly precise and reproducible manner by the creation of the deburring face defined as described. In particular when the milling is carried out by a machine, in particular in a computer-controlled manner, process fluctuations that occur in hand-guided machining processes of instrument body parts and are thus unavoidable can therefore be eliminated or at least significantly reduced. The milling also has the advantage, in particular, that the reshaped instrument body part blank cannot be excessively heated, like when machining same for removing the burrs by means of belt grinding. In addition, a deburring face that is clearly visible is created on the instrument or the at least one instrument body part, which deburring face is still clearly visible after further optional processing steps like, e.g., polishing or blasting. A deburring face of that kind with an alignment defined as proposed is thus not achievable by means of hand-guided machining processes. Overall, medical instruments with high quality and significantly improved reproducibility can thus be formed.

It is advantageous if the at least one deburring face is of self-enclosed configuration. Such a face can be created in one machining step by running down the reshaped instrument body part blank with a milling tool. In particular, this can be achieved in a simple manner by computer-supported milling. In the case of instrument body parts, self-enclosed deburring faces can be created, in particular in the region of finger rings, which are also referred to as eyes.

It is advantageous if the at least one deburring face is of planar configuration in sections and/or is configured to be convexly curved facing away from the at least one instrument body part in sections and/or is configured to be concavely curved facing away from the at least one instrument body part.

Such a deburring face can, in particular continuously, i.e., each portion thereof, be configured perpendicular to the machining plane and thus parallel to the deburring longitudinal axis. An improved reproducibility and a defined configuration of the at least one deburring face are possible in this way. In addition, any curvatures of the at least one deburring face can be achieved.

It is favorable if the at least one deburring face that is curved in sections is configured to be curved in only one dimension, and if a radius of curvature of the deburring face is defined exclusively in relation to the deburring longitudinal axis. In other words, the at least one deburring face that is curved in sections can be described as a band-shaped face that extends perpendicularly to the machining plane and thus in parallel to the deburring longitudinal axis.

The radius of curvature is preferably constant in sections or changes in sections of continuously along the extent of the at least one deburring face. Thus, deburring faces that are curved in any way, in particular one-dimensionally curved in any way, can be configured.

In accordance with a further preferred embodiment of the disclosure, provision may be made that at least two face portions of the at least one deburring face extend in parallel or substantially in parallel to one another. For example, two deburring faces may define planar face portions that extend in parallel to one another. In particular, this may be achieved on elongated branches, also referred to as arms of medical instruments. Portions of that kind may, in particular, in the case of medical instruments that comprise two instrument body parts which are pivotably held on one another, be formed on the proximal side of a joint or joint region connecting the instrument body parts, which joint region is also referred to as a closure region. In particular, said portions may extend between the closure region and finger rings or eyes of the instrument body parts.

A medical instrument can be configured in a simple manner if the at least one instrument body part is formed from the instrument body part blank by cold shaping. Additionally, very stable instrument body parts can thus be created.

It is favorable if the medical instrument comprises two instrument body parts and if the two instrument body parts are mounted on one another so as to be pivotable about a pivot axis. This configuration enables, in particular, the formation of medical instruments, for example in the form of scissors, clamps, needle holders or the like. In particular, two tool elements that are moveable relative to one another and cooperate with one another may be provided on the instrument, wherein, e.g., each of the two instrument body parts may comprise or bear a tool element.

The production of the medical instrument can be simplified, in particular, by the pivot axis defining the deburring longitudinal axis. For example, the pivot axis may be defined by a joint pin that is arranged or formed on one of the two instrument body parts. The other one of the two instrument body parts can then be moveably mounted or supported on the joint pin. For example, such a joint pin may be inserted into a bore of the instrument body part, wherein the joint pin is then permanently connected to one of the two instrument body parts, for example by adhesion or welding. The particular alignment of the pivot axis in such a way that it is defined by the deburring longitudinal axis, i.e., extending perpendicular to the machining plane, has the advantage, in particular, that such a bore for a joint pin can be formed on the instrument body parts in a simple manner in particular when the instrument body part is held and the milling tool is moved relative to the instrument body part. Thus, both the deburring face and a bore defining the pivot axis can be formed on one or both instrument body parts in one step. In particular, such an exact alignment of the pivot axis of the instrument relative to the at least one deburring face shows particularly well that the instrument body part was not deburred by a hand-guided processing operation, but rather with a machine.

To reduce a risk of injury for a user of the instrument, it is advantageous if the at least one instrument body part is polished. In particular, it may be polished by vibratory grinding. Final corners and edges can thus be removed or rounded in a defined manner.

In order to give the medical instrument a characteristic surface, it is favorable if the at least one instrument body part is blasted. In particular, it may be blasted by sandblasting or shot peening.

In order to be able to form a particularly stable medical instrument, it is favorable if the at least one instrument body part is made of a metallic material. In particular, it may be made of an instrument steel.

The present disclosure further relates to a method for producing a medical instrument, which comprises at least one instrument body part, in which method an instrument body part blank is reshaped and burrs that were created during forming, in particular due to tolerance and process fluctuations, are removed, wherein the burrs are removed by milling, in particular machine milling, wherein the at least one instrument body part is held during milling, wherein a milling tool, for the purpose of removing the burrs, is rotated about a deburring longitudinal axis and, for the purpose of creating at least one deburring face, is moved in a machining plane, the normal of which defines the deburring longitudinal axis, without changing an alignment of the deburring longitudinal axis relative to the machining plane, wherein formed on the at least one instrument body part is a joint bore with a bore longitudinal axis, said axis extending in parallel or substantially in parallel to the deburring longitudinal axis, wherein at least two, in particular only two, instrument body parts are coupled to one another so as to be pivotable with one another about the bore longitudinal axis, and wherein the medical instrument is produced in form of scissors, a plier, a needle holder or a clamp.

In the described method, burrs are thus not removed like in the prior art by hand-guided belt grinding, but rather by milling. Further, the milling is performed in a particular way by the milling tool being rotated about the deburring longitudinal axis. The machining plane thus extends perpendicularly to the deburring longitudinal axis. The reshaped instrument body part blank is held during the entire milling process, in particular, in a defined manner relative to the milling tool, namely preferably such that the machining plane does not change in its alignment relative to the deburring longitudinal axis nor to the instrument body part blank. In this way, it is possible, in particular, to create an instrument body part as described above, in which each portion of the at least one deburring face extends perpendicularly to the common machining plane, wherein the normal to the machining plane defines the deburring longitudinal axis, so that the at least one deburring face extends in parallel to the deburring longitudinal axis. The instrument body part blank can thus be clamped, e.g., in a machine in order to hold said instrument body part blank, the milling tool then being guided in the defined alignment along the instrument body part blank. This may take place, e.g., in a hand-guided manner with the support of a guidance device, or completely automatically with a CNC mill. The deburring of the at least one instrument body part may in this way take place fully automatically by a machine.

The removal of the burrs is favorably performed in a computer-controlled manner. Thus, in particular, a particularly high reproducibility can be achieved in the formation of instrument body parts. A computer-controlled milling for removing the burrs also has the advantage that no elaborate guidance devices are necessary. A computer-controlled mill can, in particular, be programmed arbitrarily, in order to thus form any deburring faces.

A part of the instrument body part is preferably also removed during removal of the burrs for forming the at least one deburring face. This is to be understood, in particular, in that not only burrs created during the forming of the instrument body part blank are removed, but a part of the instrument body part is also removed. Instrument body parts can thus be created in a highly precise form and in a highly defined manner. In addition, a width of the at least one deburring face can thus be provided in such a way that said deburring face is clearly visible to a user. Thus, in particular, instruments that are produced according to the described production method can be differentiated in a simple and secure manner from medical instruments that were deburred by means of hand-guided processing procedures.

A medical instrument can be formed in a simple and cost-effective manner if the instrument body part blank is made from a plate by punching or cutting. In particular, an instrument body part blank can be separated out of a plate by laser cutting. Thus, in particular, instrument body part blanks can be created in a defined and reproducible manner.

Particularly stable medical instruments with long service lives can be formed, in particular, by the at least one instrument body part being made of a metallic material. In particular, it may be made of an instrument steel.

The instrument body part blank is favorably reshaped by cold forming. In particular, this can be achieved by inserting the instrument body part blank into press forming tools. The instrument body part blank may be dimensioned, in particular, such that an all-round or substantially all-round burr is created during forming. This facilitates, in particular, the machining of the instrument body part after forming to remove the burrs. In particular, defined deburring faces can thus be formed.

It is favorable if the instrument body part blank is formed to a final contour of the at least one instrument body part, the burrs that are created projecting beyond the final contour. This approach can ensure, in particular, that the desired final contour of the instrument body part can be maintained, even after removing the burrs.

Further, it may be advantageous if at least one contiguous burr is created when forming the instrument body part blank. Such a burr can be removed by a traveling movement of the milling tool in one machining step.

It is favorable if formed on the at least one instrument body part is a joint bore with a bore longitudinal axis that extends in parallel or substantially in parallel to the deburring longitudinal axis. This can be achieved, in particular, in a simple manner if the reshaped instrument body part that is held for deburring is provided with the bore. Thus, in particular, a highly precise alignment of the bore longitudinal axis, which, in particular, defines the pivot axis of a medical instrument comprising two instrument body parts, relative to the at least one deburring face is achieved. In particular, such an alignment is an unmistakable indication of a medical instrument having been created in accordance with the proposed method.

Preferably at least two, in particular only two, instrument body parts are coupled to one another so as to be pivotable about the bore longitudinal axis. Scissors, pliers, needle holders, clamps or the like can thus be formed in a simple manner.

It is advantageous if, for the purpose of pivotably coupling the two instrument body parts, a common joint pin is inserted into the joint bores and is permanently connected to one of the two instrument body parts. In particular, the joint pin may be connected to one of the two instrument body parts in a force- and/or positive-locking and/or materially bonded manner. For example, a connection by adhesion or welding may take place. Thus, in particular, a permanent and defined moveable coupling of the two instrument body parts to one another can be achieved.

In order to minimize the risk of injury when handling the medical instrument, it is favorable if the at least one instrument body part is polished. In particular, it may be polished by vibratory grinding. Minimal edges and remaining burrs can thus be removed, in particular in the transition region to the at least one deburring face. In addition, an overall visual impression of the medical instrument can be improved in this way.

In order to give the medical instrument a characteristic surface, it is advantageous if the at least one instrument body part is blasted after polishing. In particular, it may be processed by sandblasting or shot peening.

Furthermore, the use of one of the methods described above for producing one of the medical instruments described above is proposed.

The instrument 10 comprises two instrument body parts 18 and 20 that are coupled to one another in a closure region 14 so as to be pivotable about a pivot axis 16.

The closure region 14 is configured in the form of a push-through closure with a substantially cuboidal closure box 24 that has a slot 22. On the closure box 24, a joint pin 26 passing through the slot 22, the longitudinal axis of said joint pin 26 defining the pivot axis 16, is inserted into a joint bore 28 that also defines the pivot axis and is immovably fixed to the closure box 24.

A joint bore that is not depicted in the Figures is also formed on a closure portion 30 of the instrument body part 20, said joint bore being passed through by the joint pin 26 when the closure portion 30 passes through the slot 22.

The instrument body parts 18 and 20 each have deburring faces 32 and 34. All deburring faces 32 and 34 extend in parallel to the pivot axis 16 and thus perpendicularly to a machining plane 36. The pivot axis 16 defines a normal 38 to the machining plane 36.

Distal ends of the instrument body parts 18, 20 form tool elements 40 and 42, respectively. In the case of the towel clamp, said tool elements are configured in the form of tips pointing toward one another. However, they may also be configured in the form of cutting edges or blunt clamping elements in order to configure an instrument 10 in the form of scissors or a blunt clamp or a needle holder.

From the closure region 14, branches 44 and 46 extend in the proximal direction up to self-enclosed finger rings 48 and 50, respectively.

Directly on the distal side of the finger rings 48 and 50 are locking elements 52 and 54, respectively, which are each toothed and together form a locking device 56 in order to hold the instrument 10 in a defined closing state.

The deburring faces 34 in the region of the finger rings 48 and 50 are configured to be concavely curved facing away from the respective finger ring 48 or 50 and are of self-enclosed configuration. A radius of curvature of the deburring faces 34 changes continuously. Optionally, the finger rings 48 and 50, which in the embodiment depicted in FIG. 12 have an oval shape in plan view, may also be of annular configuration and have a constant radius of curvature.

Face portions 84 and 86 of the deburring faces 32 in the region of the branches 44 and 46 between the closure region 14 and the locking elements 52 and 54, respectively, are of planar or substantially planar configuration and extend in parallel or substantially in parallel to one another at least in sections.

The deburring faces 32 in the region of the finger rings 48 and 50 are concavely curved facing away from the respective instrument body part 18 and 20.

As already explained, each deburring face 32 and 34 comprises one or more portions, all portions of the deburring faces 32 and 34 extending perpendicularly to the common machining plane 36.

The production of the instrument 10 is described in more detail in the following in connection with FIGS. 1 to 12.

Instrument body part blanks 58 are reshaped to create the instrument body parts 18 and 20.

FIG. 1 shows for example an instrument body part blank 58 punched or cut out of a plate 60 by punching or laser cutting, from which blank both the instrument body part 18 and the instrument body part 20 can be formed.

FIG. 2 shows schematically a cut view of the plate 60 along line 2-2 with the cut out instrument body part blank 58.

The instrument body part blank 58 is formed to create one of the instrument body parts 18 and 20. FIG. 3 shows schematically two forming tools 62 and 64, each with a receptacle 66 and 68, respectively, corresponding to a final contour for forming an upper and a lower half of the instrument body part 18 and 20, respectively.

The instrument body part blank 58 is inserted into the receptacles 66 and 68 of the forming tools 62 and 64 and the forming tools 62 and 64 are then pressed against one another. The instrument body part 18 is created through the described cold forming of the instrument body part blank 58 made of a metallic material, and has substantially its final contour.

The forming tools 62 and 64 are configured such that by being pressed together, they form the instrument body part 18 with burrs 70 projecting on all sides. The burrs 70 point in parallel to the machining plane 36.

The cold forming is preferably performed such that the burrs 70 that are created are self-enclosed. Schematically depicted in FIG. 6 for example in the case of the instrument body part 18 are two burrs 70 of self-enclosed configuration.

The protruding burrs 70 are removed, namely by milling. For this purpose, the instrument body part 18 is machined. A milling tool 72 is rotated by a drive 74 about a deburring longitudinal axis 76. The drive 74 is controlled by a control device 78 that is in control-operative connection with said drive 74 in order to move the drive 74 with the milling tool 72 in a desired manner. The drive 74 moves the milling tool 72 on the instrument body part 18 in a defined, predetermined manner in order to remove the projecting burrs 70.

During deburring, the milling tool 72 is moved in such a way that the deburring longitudinal axis is always oriented perpendicularly to the machining plane 36. The deburring longitudinal axis 76 maintains this orientation relative to the machining plane 36 during the entire deburring process.

During deburring, the instrument body part 18 is held with a holding device 80, which is schematically depicted in FIG. 8. In this way, an orientation or alignment of the deburring longitudinal axis 76 relative to the instrument body part 18 can be maintained in a simple manner.

Upon removal of the burrs 70 with the milling tool 72, not only the burrs 70 but also a part of the instrument body part 18 are removed for forming the deburring faces 32 and 34, which are oriented perpendicularly to the machining plane 36 in the described manner.

The instrument body part 18 held with the holding device 80 is provided in the region of the closure box 24 with the joint bore 28 oriented perpendicularly to the machining plane 36. Further, the slot 22 oriented in parallel to the machining plane 36 is formed.

As can be easily seen in particular in FIG. 10, the deburring faces 32 extend in parallel to the pivot axis 16.

This results directly from the orientation of the milling tool 72 with its deburring longitudinal axis 76.

The instrument body part 18 may optionally be polished, as schematically depicted in FIG. 11. To this end, FIG. 11 shows a polishing tool 82 with which non-rounded transitions on the instrument body part 18 that arise as a result of the deburring are rounded.

Alternatively to polishing with the polishing tool 82, the deburred instrument body parts 18 may also be polished by vibratory grinding in a vibratory grinding installation.

The instrument body parts 18 and 20 can then be treated by blasting, for example by sandblasting or ball peening. A defined and aesthetically pleasing surface of the instrument body parts 18 and 20 can thus be achieved.

The instrument body parts 18 and 20 configured as described can then be connected to the joint pin 26, as explained at the outset, to form the instrument 10.

In the described manner, different medical instruments can be formed, for example scissors, clamps, needle holders, or pliers. The instruments are configured with corresponding tool elements for the respective intended purpose.

The described production method enables a nearly complete production of instruments 10 purely by machine. In particular, CNC mills may be used for deburring the instrument body parts 18 and 20 after the forming from instrument body part blanks 58. This enables a high reproducibility and thus a consistently high quality of the instruments 10.

The described production method enables, in particular, a secure identification of instruments 10 that are configured according to the described method. The alignment of the pivot axis 16 relative to the deburring faces 32 and 34 can be achieved in a highly precise manner due to the processing by machine, which, in particular, is not possible by hand-guided machining steps like hand-guided belt grinding of the reshaped instrument body part blanks 58 for removing the burrs 70.

The removal of the burrs 70 was described above with a milling tool 72 that is configured in the form of a peripheral milling cutter. In principle, it is also possible to form the deburring faces 32 and 34 with a milling tool 62 in the form of an end milling cutter. However, an end milling cutter is then not oriented with the deburring longitudinal axis 76 perpendicular to the machining plane 36, but rather in parallel thereto. Said end milling cutter is thus rotated about an axis that extends in parallel to the machining plane 36, in particular lying therein. In this case, a deburring longitudinal axis 76 can also be defined, in parallel to which all deburring faces 32 and 34 on the instrument 10 extend and which is oriented perpendicularly to the machining plane 36.

The invention claimed is:

1. A method for producing a medical instrument that comprises a first instrument body part and a second instrument body part, the method comprising the steps of reshaping an instrument body part blank and removing one or more burrs created during forming, wherein the first instrument body part defines a first perimeter extending within a first plane and the second instrument body part defines a second perimeter extending within a second plane, the first instrument body part being produced with one or more burrs during reshaping that extend along the first perimeter, the second instrument body part being produced with one or more burrs during reshaping that extend along the second perimeter, wherein one or more burrs are removed from the first instrument body part by moving a milling tool completely around the first perimeter of the first instrument body part, wherein one or more burrs are removed from the second instrument body part by moving the milling tool completely around the second perimeter of the second instrument body part, wherein each of the first instrument body part and the second instrument body part is held in a holding device, separate from one another, during milling, wherein the milling tool is rotated about a deburring longitudinal axis for removing the one or more burrs, and the milling tool is moved in a machining plane for creating at least one deburring face, a normal of the machining plane defining the deburring longitudinal axis, without changing an alignment of the deburring longitudinal axis relative to the machining plane, wherein, after the one or more burrs are removed, a first joint bore having a first bore longitudinal axis is formed in the first instrument body part while the first instrument body part is still held in the holding device, and a second joint bore having a second bore longitudinal axis is formed the second instrument body part while the second instrument body part is still held in the holding device, the first bore longitudinal axis and the second bore longitudinal axis each extending in parallel to the deburring longitudinal axis, wherein the first instrument body part provided with the first joint bore is coupled to the second instrument body part provided with the second joint bore so as to be pivotable relative to the second instrument body part about the first bore longitudinal axis, and wherein the medical instrument is one of scissors, a plier, a needle holder or a clamp.

2. The method according to claim 1, wherein removal of the one or more burrs is performed in a computer-controlled manner.

3. The method according to claim 1, wherein during removal of the one or more burrs, a part of the first instrument body part is removed for creating the at least one deburring face.

4. The method according to claim 1, wherein the instrument body part blank is at least one of:
   a) made from a plate by punching or cutting;
   b) made of a metallic material;
   c) reshaped by cold forming; and
   d) reshaped to a final contour of the first instrument body part, the one or more burrs projecting beyond the final contour.

5. The method according to claim 1, wherein the one or more burrs comprises at least one contiguous burr that is created during forming of the instrument body part blank.

6. The method according to claim 1, wherein for pivotably coupling the first instrument body part and the second instrument body part, a common hinge pin is inserted into the first joint bore and the second joint bore, and is permanently connected to one of the first instrument body part and the second instrument body part.

7. The method according to claim 1, wherein the first instrument body part is polished.

8. The method according to claim 7, wherein the first instrument body part is at least one of:
   a) polished after removing all of the one or more burrs; and
   b) blasted.

9. A method for producing a medical instrument comprising the steps of:
   removing material from a first plate to form a first instrument body part blank;
   removing material from a second plate to form a second instrument body part blank;
   placing the first instrument body part blank in at least one forming tool, the at least one forming tool comprising a first forming tool part defining a first recess and a second forming tool part defining a second recess, the first recess and the second recess collectively defining a receptacle for receiving the first instrument body part blank between the first forming tool part and the second forming tool part, with a perimeter surface of the first instrument body part blank aligned with a gap between the first forming tool part and the second forming tool part;

pressing the first forming tool part and the second forming tool part together to reshape the first instrument body part blank and displace material of the first instrument body part blank into the gap between the first forming tool part and the second forming tool part to create one or more burrs along the perimeter surface of the first instrument body part blank;

placing the second instrument body part blank in the at least one forming tool, with a perimeter surface of the second instrument body part blank aligned with the gap between the first forming tool part and the second forming tool part;

pressing the first forming tool part and the second forming tool part together to reshape the second instrument body part blank and displace material of the second instrument body part blank into the gap between the first forming tool part and the second forming tool part to create one or more burrs along the perimeter surface of the second instrument body part blank;

removing the first instrument body part blank from the at least one forming tool;

removing the second instrument body part blank from the at least one forming tool;

placing the first instrument body part blank in at least one holding device;

machining the first instrument body part blank to remove one or more burrs by advancing a rotating milling tool along the perimeter surface of the first instrument body part blank, the rotating milling tool being confined within a first machining plane and rotatable about a deburring axis that remains perpendicular to the first machining plane;

forming a first joint bore in the first instrument body part blank while the first instrument body part blank is still held in the at least one holding device and separate from the second instrument body part blank, so as to form a first instrument body part;

removing the first instrument body part from the at least one holding device;

placing the second instrument body part blank in the at least one holding device;

machining the second instrument body part blank to remove one or more burrs by advancing the rotating milling tool along the perimeter surface of the second instrument body part blank, the rotating milling tool being confined within a second machining plane and rotatable about the deburring axis that remains perpendicular to the second machining plane; and forming a second joint bore in the second instrument body part blank while the second instrument body part blank is still held in the at least one holding device separate from the first instrument body part blank, so as to form a second instrument body part; and removing the second instrument body part from the at least one holding device.

10. The method for producing the medical instrument according to claim 9, wherein the first instrument body part and the second instrument body part have different geometries.

11. The method for producing the medical instrument according to claim 10, wherein the first instrument body part blank and the second instrument body part blank have identical sizes and shapes, such that the first instrument body part and the second instrument body part are formed from a common blank geometry.

12. The method for producing the medical instrument according to claim 9, wherein the perimeter surface of the first instrument body part blank extends along an outside periphery of the first instrument body part blank.

13. The method for producing the medical instrument according to claim 9, wherein the perimeter surface of the first instrument body part blank extends inside a ring section of the first instrument body part blank.

14. The method for producing the medical instrument according to claim 9, further comprising the step of aligning the first joint bore of the first instrument body part with the second joint bore of the second instrument body part.

15. The method for producing the medical instrument according to claim 14, further comprising the step of pivotally coupling the first instrument body part to the second instrument body part to form the medical instrument.

* * * * *